US008442776B2

(12) United States Patent
Lambris et al.

(10) Patent No.: US 8,442,776 B2
(45) Date of Patent: May 14, 2013

(54) STRUCTURE OF COMPSTATIN-C3 COMPLEX AND USE FOR RATIONAL DRUG DESIGN (75) Inventors: John D. Lambris, Bryn Mawr, PA (US); Bert J. C. Janssen, Oxford (GB); Piet Gros, Utrecht (NL)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/663,544

(22) PCT Filed: Jun. 6, 2008

(86) PCT No.: PCT/US2008/007152
§ 371 (c)(1),
(2), (4) Date: Aug. 12, 2010

(87) PCT Pub. No.: WO2008/153963
PCT Pub. Date: Dec. 18, 2008

(65) Prior Publication Data
US 2011/0060127 A1   Mar. 10, 2011

Related U.S. Application Data (60) Provisional application No. 60/933,933, filed on Jun. 8, 2007.

(51) Int. Cl.
*G01N 33/00*    (2006.01)

(52) U.S. Cl.
USPC ............................................ 702/27; 436/86

(58) Field of Classification Search ....................... None
See application file for complete search history.

(56) References Cited

U.S. PATENT DOCUMENTS

| 6,319,897 | B1 | 11/2001 | Lambris et al. |
| 2003/0036093 | A1 | 2/2003 | Floudas et al. |
| 2005/0079585 | A1 | 4/2005 | Kolln et al. |
| 2005/0143402 | A1* | 6/2005 | Cheetham et al. ....... 514/266.21 |

FOREIGN PATENT DOCUMENTS

| WO | WO 99/13899 A1 | 3/1999 |
| WO | WO 2004/026328 A1 | 4/2004 |
| WO | WO 2007/062249 A2 | 5/2007 |
| WO | WO 2008/153963 A1 | 12/2008 |

OTHER PUBLICATIONS

Wiencek, J. M. New Stratigies for Protein Crystal Growth. Ann. Rev. Biomed. Eng. 1999, 1, 505-534.*
Bruijn et al. Proc. Natl. Acad. Sci. USA (1985) 82, 708-712.*
Bohm, H.J., "The computer program LUDI: a new method for the de novo design of enzyme inhibitors", J. Comput. Aided Mol. Des., vol. 6, pp. 61-78 (1992).
Bokisch, V.A., et al., "Isolation of a fragment (C3a) of the third component of human complement containing anaphylatoxin . . . ", J. Exp. Med., vol. 129, pp. 1109-1130 (1969).

(Continued)

*Primary Examiner* — Nashaat Nashed
(74) *Attorney, Agent, or Firm* — Potter Anderson & Corroon, LLP (57) ABSTRACT

The structure of C3c in complex with the complement inhibitor, compstatin, and use of this information for rational design or identification of complement-inhibiting drugs are disclosed.

11 Claims, 4 Drawing Sheets
(4 of 4 Drawing Sheet(s) Filed in Color)

OTHER PUBLICATIONS

Bureeva, S., et al., "Drug design using the example of the complement system inhibitors' development", Drug Discov. Today, vol. 10, pp. 1535-1542 (2005).
Carroll, M.C., et al., "The complement system in regulation of adaptive immunity", Nat. Immunol., vol. 5, pp. 981-986 (2004).
CCP4, "The CCP4 suite: programs for protein crystallography", Acta. Crystallogr. D. Biol. Crystallogr., vol. 50, pp. 760-763.
Duan, Y., et al., "Physiochemical and residue conservation calculations to improve the ranking of protein-protein docking solutions", Protein Sci., vol. 14, pp. 316-328 (2005).
Eisen, M.B., et al., "HOOK: A program for finding novel molecular architectures that satisfy the . . . ", Proteins: Structure, Function, and Genetics, vol. 19, pp. 199-221 (1994).
Emsley, P., et al., "Coot: model-building tools for molecular graphics", Acta. Crystallogr. D. Biol. Crystallogr., vol. 60, pp. 2126-2132 (2004).
Fredslund, F., et al., "The structure of bovine complement component 3 reveals the basis for thioester function", J. Mol. Biol., vol. 361, pp. 115-127 (2006).
Furlong, S.T., et al., "C3 activation is inhibited by analogs of compstatin but not by serine protease . . . ", Immunopharmacology, vol. 48, pp. 199-212 (2000).
Hammel, M., et al., "A structural basis for complement inhibition by *Staphylococcus aureus*", Nat. Immunol., vol. 8, pp. 430-437 (2007).
Holland, M.C., et al., "Synthetic small-molecule complement inhibitors", Curr. Opin. Investig. Drugs, vol. 5, pp. 1164-1173 (2004).
Janssen, B.J., et al., "Structures of complement component C3 provide insights into the function and evolution of immunity", Nature, vol. 437, pp. 505-511 (2005).
Janssen, B.J., et al., "Structure of Cb3 reveals conformational changes that underlie complement activity", Nature, vol. 444, pp. 213-216 (2006).
Janssen, B.J., et al., "Structural insights into the central complement component C3", Mol. Immunol., vol. 44, pp. 213-216 (2007).
Katragadda, M., et al., "Thermodynamic studies on the interaction of the third complemen . . . ", J. Biol. Chem., vol. 279, pp. 54987-54995 (2004).
Katragadda, M., et al., "Hydrophobic effect and hydrogen bonds account for the improve . . . ", J. Med. Chem., vol. 49, pp. 4616-4622 (2006).
Lauri, G., et al., "Caveat: a program to facilitate the design of organic molecules", J. Comput. Aided Mol. Des., vol. 8, pp. 51-66 (1994).
Luty, B.A., et al., "Molecular mechanics/grid method for evaluation of ligan-receptor interactions", J. Comput. Chem., vol. 16, pp. 454-464 (1995).
Mallik, B., et al., "Design and NMR characterization of active analogues of compstatin . . . ", J. Med. Chem., vol. 48, pp. 274-286 (2005).
McCoy, A.J., et al., "Likelihood-enhanced fast translation functions", Acta. Crystallogr. D. Biol. Crystallogr., vol. 61, pp. 458-464 (2005).
Morikis, D., et al., "Solution structure of Compstatin, a potent complement inhibitor", Protein Sci., vol. 7, 619-627 (1998).
Morikis, D., et al., "The structural basis of compstatin activity examined by structure-function-base . . . ", J. Biol. Chem., vol. 277, pp. 14942-14953 (2002).
Morikis, D., et al., "Improvement of the anti-C3 activity of compstatin using rational and combinatorial approaches", Biochem. Soc. Trans., vol. 32, pp. 28-32 (2004).
Morris, G.M., et al., "Automated docking using a Lamarckian genetic algorithm and an empirica . . . ", J. Computational Chem., vol. 19, pp. 1639-1662 (1998).
Nishida, N., et al., "Structural transitions of complement component C3 and its activation products", Proc. Natl. Acad. Sci. USA, vol. 103, pp. 19737-19742 (2006).
Ponnuraj, K., et al., "Structural analysis of engineered Bb fragment of complement factor B: insights into . . . ", Mol. Cell, vol. 14, pp. 17-28 (2004).
Sahu, A., et al., "Inhibition of human complement by a C3-binding peptide isolated from a phage . . . ", J. Immunol., vol. 157, pp. 884-891 (1996).
Sahu, A., et al., "Complement inhibitors: a resurgent concept in anti-inflammatory therapeutics", Immunopharmacology, vol. 49, pp. 133-148 (2000).
Sahu, A., et al., "Binding kinetics, structure-activity relationship, and biotransformation of the complemen . . . ", J. Immunol., vol. 165, pp. 2491-2499 (2000).
Sahu, A., et al., "Compstatin, a peptide inhibitor of complement, exhibits species-specific binding to . . . ", Mol. Immunol., vol. 39, pp. 557-566 (2003).
Soulika, A.M., et al., "Studies of structure-activity relation of complement inhibitor compstatin", J. Immunol., vol. 171, pp. 1881-1890 (2003).
Soulika, A.M., et al., "Compstatin, inhibits complement activation by binding to the beta-chain of complement factor 3", Mol. Immunol., vol. 43, pp. 2023-2029 (2006).
Stouten, P.F., et al., "An effective solvation term based on atomic occupancies for use in protein simulations", Molecular Simulation, vol. 10, pp. 97-120 (1993).
Thompson, J.D., et al., "CLUSTAL W: improving the sensitivity of progressive multiple sequence alignment . . . ", Nucleic Acids Res., vol. 22, pp. 4673-4680 (1994).
Vicatos, S., et al., "Prediction of distant residue contacts with the use of evolutionary information", Proteins, vol. 58, pp. 935-949 (2005).
Wallace, A.C., et al., "LIGPLOT: a program to generate schematic diagrams of protein-ligand interactions", Protein Eng., vol. 8, pp. 127-134 (1995).
Walport, M.J., "Complement. First of two parts", New Engl. J. Med., vol. 344, pp. 1058-1066 (2001).
Wiesmann, C., et al., "Structure of C3b in complex with CRIg gives insights into regulation of complement activation", Nature, vol. 444, pp. 217-220 (2006).
International Search Report and Written Opinion in PCT/US2008/007152, mailed Sep. 8, 2008.

* cited by examiner

SEQUENCE LISTING

<160> NUMBER OF SEQ ID NOS: 4

<210> SEQ ID NO 1
<211> LENGTH: 13
<212> TYPE: PRT
<213> ORGANISM: Artificial sequence
<220> FEATURE:
<223> OTHER INFORMATION: synthetic sequence

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (13)..(13)
<223> OTHER INFORMATION: AMIDATION

<400> SEQUENCE: 1

Ile Cys Val Trp Gln Asp Trp Gly Ala His Arg Cys Thr
1               5                   10

<210> SEQ ID NO 2
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (2)..(12)

<400> SEQUENCE: 2

Ile Cys Val Val Gln Asp Trp Gly His His Arg Cys Thr
1               5                   10

<210> SEQ ID NO 3
<211> LENGTH: 643
<212> TYPE: PRT
<213> ORGANISM: Homo sapiens

<400> SEQUENCE: 3

Ser Pro Met Tyr Ser Ile Ile Thr Pro Asn Ile Leu Arg Leu Glu Ser
1               5                   10                  15

Glu Glu Thr Met Val Leu Glu Ala His Asp Ala Gln Gly Asp Val Pro
            20                  25                  30

Val Thr Val Thr Val His Asp Phe Pro Gly Lys Lys Leu Val Leu Ser
        35                  40                  45

Ser Glu Lys Thr Val Leu Thr Pro Ala Thr Asn His Met Gly Asn Val
    50                  55                  60

Thr Phe Thr Ile Pro Ala Asn Arg Glu Phe Lys Ser Glu Lys Gly Arg
65                  70                  75                  80

Asn Lys Phe Val Thr Val Gln Ala Thr Phe Gly Thr Gln Val Val Glu
                85                  90                  95

Lys Val Val Leu Val Ser Leu Gln Ser Gly Tyr Leu Phe Ile Gln Thr
            100                 105                 110

Asp Lys Thr Ile Tyr Thr Pro Gly Ser Thr Val Leu Tyr Arg Ile Phe
        115                 120                 125

Thr Val Asn His Lys Leu Leu Pro Val Gly Arg Thr Val Met Val Asn
    130                 135                 140

Ile Glu Asn Pro Glu Gly Ile Pro Val Lys Gln Asp Ser Leu Ser Ser
145                 150                 155                 160

Gln Asn Gln Leu Gly Val Leu Pro Leu Ser Trp Asp Ile Pro Glu Leu
                165                 170                 175

Val Asn Met Gly Gln Trp Lys Ile Arg Ala Tyr Tyr Glu Asn Ser Pro
            180                 185                 190

Gln Gln Val Phe Ser Thr Glu Phe Glu Val Lys Glu Tyr Val Leu Pro
        195                 200                 205
```

```
Ser Phe Glu Val Ile Val Glu Pro Thr Glu Lys Phe Tyr Ile Tyr
    210                 215                 220

Asn Glu Lys Gly Leu Glu Val Thr Ile Thr Ala Arg Phe Leu Tyr Gly
225                 230                 235                 240

Lys Lys Val Glu Gly Thr Ala Phe Val Ile Phe Gly Ile Gln Asp Gly
                245                 250                 255

Glu Gln Arg Ile Ser Leu Pro Glu Ser Leu Lys Arg Ile Pro Ile Glu
            260                 265                 270

Asp Gly Ser Gly Glu Val Val Leu Ser Arg Lys Val Leu Leu Asp Gly
        275                 280                 285

Val Gln Asn Leu Arg Ala Glu Asp Leu Val Gly Lys Ser Leu Tyr Val
    290                 295                 300

Ser Ala Thr Val Ile Leu His Ser Gly Ser Asp Met Val Gln Ala Glu
305                 310                 315                 320

Arg Ser Gly Ile Pro Ile Val Thr Ser Pro Tyr Gln Ile His Phe Thr
                325                 330                 335

Lys Thr Pro Lys Tyr Phe Lys Pro Gly Met Pro Phe Asp Leu Met Val
            340                 345                 350

Phe Val Thr Asn Pro Asp Gly Ser Pro Ala Tyr Arg Val Pro Val Ala
        355                 360                 365

Val Gln Gly Glu Asp Thr Val Gln Ser Leu Thr Gln Gly Asp Gly Val
    370                 375                 380

Ala Lys Leu Ser Ile Asn Thr His Pro Ser Gln Lys Pro Leu Ser Ile
385                 390                 395                 400

Thr Val Arg Thr Lys Lys Gln Glu Leu Ser Ala Glu Gln Ala Thr
                405                 410                 415

Arg Thr Met Gln Ala Leu Pro Tyr Ser Thr Val Gly Asn Ser Asn Asn
            420                 425                 430

Tyr Leu His Leu Ser Val Leu Arg Thr Glu Leu Arg Pro Gly Glu Thr
        435                 440                 445

Leu Asn Val Asn Phe Leu Leu Arg Met Asp Arg Ala His Glu Ala Lys
    450                 455                 460

Ile Arg Tyr Tyr Thr Tyr Leu Ile Met Asn Lys Gly Arg Leu Leu Lys
465                 470                 475                 480

Ala Gly Arg Gln Val Arg Glu Pro Gly Gln Asp Leu Val Val Leu Pro
                485                 490                 495

Leu Ser Ile Thr Thr Asp Phe Ile Pro Ser Phe Arg Leu Val Ala Tyr
            500                 505                 510

Tyr Thr Leu Ile Gly Ala Ser Gly Gln Arg Glu Val Val Ala Asp Ser
        515                 520                 525

Val Trp Val Asp Val Lys Asp Ser Cys Val Gly Ser Leu Val Val Lys
    530                 535                 540

Ser Gly Gln Ser Glu Asp Arg Gln Pro Val Pro Gly Gln Gln Met Thr
545                 550                 555                 560

Leu Lys Ile Glu Gly Asp His Gly Ala Arg Val Val Leu Val Ala Val
                565                 570                 575

Asp Lys Gly Val Phe Val Leu Asn Lys Lys Asn Lys Leu Thr Gln Ser
            580                 585                 590

Lys Ile Trp Asp Val Val Glu Lys Ala Asp Ile Gly Cys Thr Pro Gly
        595                 600                 605

Ser Gly Lys Asp Tyr Ala Gly Val Phe Ser Asp Ala Gly Leu Thr Phe
    610                 615                 620

Thr Ser Ser Ser Gly Gln Gln Thr Ala Gln Arg Ala Glu Leu Gln Cys
625                 630                 635                 640
```

Pro Gln Pro

<210> SEQ ID NO 4
<211> LENGTH: 643
<212> TYPE: PRT
<213> ORGANISM: Homo sapiens

<400> SEQUENCE: 4

```
Ser Pro Met Tyr Ser Ile Ile Thr Pro Asn Ile Leu Arg Leu Glu Ser
1               5                   10                  15

Glu Glu Thr Met Val Leu Glu Ala His Asp Ala Gln Gly Asp Val Pro
            20                  25                  30

Val Thr Val Thr Val His Asp Phe Pro Gly Lys Lys Leu Val Leu Ser
        35                  40                  45

Ser Glu Lys Thr Val Leu Thr Pro Ala Thr Asn His Met Gly Asn Val
    50                  55                  60

Thr Phe Thr Ile Pro Ala Asn Arg Glu Phe Lys Ser Glu Lys Gly Arg
65                  70                  75                  80

Asn Lys Phe Val Thr Val Gln Ala Thr Phe Gly Thr Gln Val Val Glu
                85                  90                  95

Lys Val Val Leu Val Ser Leu Gln Ser Gly Tyr Leu Phe Ile Gln Thr
            100                 105                 110

Asp Lys Thr Ile Tyr Thr Pro Gly Ser Thr Val Leu Tyr Arg Ile Phe
        115                 120                 125

Thr Val Asn His Lys Leu Leu Pro Val Gly Arg Thr Val Met Val Asn
    130                 135                 140

Ile Glu Asn Pro Glu Gly Ile Pro Val Lys Gln Asp Ser Leu Ser Ser
145                 150                 155                 160

Gln Asn Gln Leu Gly Val Leu Pro Leu Ser Trp Asp Ile Pro Glu Leu
                165                 170                 175

Val Asn Met Gly Gln Trp Lys Ile Arg Ala Tyr Tyr Glu Asn Ser Pro
            180                 185                 190

Gln Gln Val Phe Ser Thr Glu Phe Glu Val Lys Glu Tyr Val Leu Pro
        195                 200                 205

Ser Phe Glu Val Ile Val Glu Pro Thr Glu Lys Phe Tyr Tyr Ile Tyr
    210                 215                 220

Asn Glu Lys Gly Leu Glu Val Thr Ile Thr Ala Arg Phe Leu Tyr Gly
225                 230                 235                 240

Lys Lys Val Glu Gly Thr Ala Phe Val Ile Phe Gly Ile Gln Asp Gly
                245                 250                 255

Glu Gln Arg Ile Ser Leu Pro Glu Ser Leu Lys Arg Ile Pro Ile Glu
            260                 265                 270

Asp Gly Ser Gly Glu Val Val Leu Ser Arg Lys Val Leu Leu Asp Gly
        275                 280                 285

Val Gln Asn Leu Arg Ala Glu Asp Leu Val Gly Lys Ser Leu Tyr Val
    290                 295                 300

Ser Ala Thr Val Ile Leu His Ser Gly Ser Asp Met Val Gln Ala Glu
305                 310                 315                 320

Arg Ser Gly Ile Pro Ile Val Thr Ser Pro Tyr Gln Ile His Phe Thr
                325                 330                 335

Lys Thr Pro Lys Tyr Phe Lys Pro Gly Met Pro Phe Asp Leu Met Val
            340                 345                 350

Phe Val Thr Asn Pro Asp Gly Ser Pro Ala Tyr Arg Val Pro Val Ala
        355                 360                 365
```

-continued

```
Val Gln Gly Glu Asp Thr Val Gln Ser Leu Thr Gln Gly Asp Gly Val
        370                 375                 380
Ala Lys Leu Ser Ile Asn Thr His Pro Ser Gln Lys Pro Leu Ser Ile
385                     390                 395                 400
Thr Val Arg Thr Lys Lys Gln Glu Leu Ser Glu Ala Glu Gln Ala Thr
                405                 410                 415
Arg Thr Met Gln Ala Leu Pro Tyr Ser Thr Val Gly Asn Ser Asn Asn
            420                 425                 430
Tyr Leu His Leu Ser Val Leu Arg Thr Glu Leu Arg Pro Gly Glu Thr
        435                 440                 445
Leu Asn Val Asn Phe Leu Leu Arg Met Asp Arg Ala His Glu Ala Lys
        450                 455                 460
Ile Arg Tyr Tyr Thr Tyr Leu Ile Met Asn Lys Gly Arg Leu Leu Lys
465                     470                 475                 480
Ala Gly Arg Gln Val Arg Glu Pro Gly Gln Asp Leu Val Val Leu Pro
                485                 490                 495
Leu Ser Ile Thr Thr Asp Phe Ile Pro Ser Phe Arg Leu Val Ala Tyr
            500                 505                 510
Tyr Thr Leu Ile Gly Ala Ser Gly Gln Arg Glu Val Val Ala Asp Ser
        515                 520                 525
Val Trp Val Asp Val Lys Asp Ser Cys Val Gly Ser Leu Val Val Lys
        530                 535                 540
Ser Gly Gln Ser Glu Asp Arg Gln Pro Val Pro Gly Gln Gln Met Thr
545                     550                 555                 560
Leu Lys Ile Glu Gly Asp His Gly Ala Arg Val Val Leu Val Ala Val
                565                 570                 575
Asp Lys Gly Val Phe Val Leu Asn Lys Lys Asn Lys Leu Thr Gln Ser
            580                 585                 590
Lys Ile Trp Asp Val Val Glu Lys Ala Asp Ile Gly Cys Thr Pro Gly
        595                 600                 605
Ser Gly Lys Asp Tyr Ala Gly Val Phe Ser Asp Ala Gly Leu Thr Phe
        610                 615                 620
Thr Ser Ser Ser Gly Gln Gln Thr Ala Gln Arg Ala Glu Leu Gln Cys
625                     630                 635                 640
Pro Gln Pro
```

STRUCTURE OF COMPSTATIN-C3 COMPLEX AND USE FOR RATIONAL DRUG DESIGN

Pursuant to 35 U.S.C. §202(c), it is acknowledged that the United States government may have certain rights in the invention described herein, which was made in part with funds from the National Institutes of Health under Grant Nos. GM 62134 and GM 069736.

FIELD OF THE INVENTION

This invention relates to activation of the complement cascade in the body. In particular, this invention provides the structure of the C3 inhibitor, compstatin, in complex with C3c, and uses of that structural information for rational drug design.

BACKGROUND OF THE INVENTION

Various publications, including patents, published applications, technical articles and scholarly articles are cited throughout the specification. Each of these cited publications is incorporated by reference herein, in its entirety. Full citations for publications not cited fully within the specification are set forth at the end of the specification.

The complement system is a key part of the innate and adaptive immune system and plays a major role in homeostasis by clearing altered host cells and invading pathogens (Carroll, 2004; Walport, 2001). Inappropriate activation of the complement system leads to tissue injury causing or aggravating various pathological conditions, such as autoimmune diseases, burn injuries, Alzheimer's disease, stroke and heart attack, among others (reviewed by Sahu and Lambris, 2000). Several complement inhibitors currently under development target various steps in the complement activation pathways. To date, none of these compounds has been approved for clinical use (Bureeva et al., 2005; Holland et al., 2004; Sahu and Lambris, 2000). Many of the substances under investigation possess the disadvantage of being a large molecular weight proteins that are difficult to manufacture and must be administered by infusion. Accordingly, ongoing research continues to emphasize the development of smaller active agents that are easier to deliver, more stable and less costly to manufacture.

U.S. Pat. No. 6,319,897 to Lambris et al. describes the use of a phage-displayed combinatorial random peptide library to identify a 27-residue peptide that binds to C3 and inhibits complement activation. This peptide was truncated to a 13-residue cyclic segment that maintained complete activity, which is referred to in the art as compstatin (SEQ ID NO: 2J. Compstatin inhibits complement response by preventing the proteolytic activation of C3 (Sahu et al., 1996). Activation of C3 by the C3 convertases is a central amplification step in complement activation. All three recognition and initiation pathways, the classical (CP), lectin (LP) and alternative (AP) pathways, converge in the activation of C3. Proteolytic activation of C3 yields C3b, which covalently binds to pathogenic or self surfaces providing a strong signal for clearance of the tagged particles. Because compstatin blocks this critical step of complement activation and because it is a small non-immunogenic peptide, compstatin has the potential to be developed into a therapeutic agent.

Compstatin (SEQ ID NO:2), a 13-residue peptide, circularized by disulfide bond (Cys-2-Cys-12), displays an inhibitory activity of $IC_{50}=12$ μM. In solution, compstatin forms a β-turn at residues Gln-5-Gly-8 with the disulfide bridge Cys-2-Cys-12, residues Ile-1-Val-4 and Thr-13 forming a hydrophobic cluster (PCT Pub. No. WO99/13899; Morikis et al., 1998; Morikis et al., 2002). Mutational studies showed that the polar β-turn and the hydrophobic cluster are essential for the inhibitory activity of compstatin (Furlong et al., 2000; Morikis et al., 1998; Morikis et al., 2002; Soulika et al., 2003). Both main-chain and side-chain atoms of compstatin are thought to be involved in interaction with C3 (Sahu et al., 2000). Recently, an analogue of compstatin with 45-fold higher potency was identified, which contained an acetylated N-terminus and amino-acid substitutions V4W and H9A (PCT Pub. No. WO2004/026328; Katragadda et al., 2004; Mallik et al., 2005) (SEQ ID NO: 1). These compounds bind C3 ($K_d$ of 1.3 μM and 0.14 μM for natural compstatin with an acetylated N-terminus and the V4W/H9A analogue respectively (Katragadda et al., 2004)) and its derived products C3($H_2O$), C3b and C3c (Sahu et al., 1996; Sahu et al., 2000). Soulika et al. (Soulika et al., 2006) showed that the binding site resides in the 40-kDa C-terminal part of the β-chain that is common to these proteins. Overall, these and other studies have led to a model in which compstatin inhibits complement activation by blocking binding of C3 to the C3 convertases, either through inducing a conformational change in C3 or causing steric hindrance when bound to C3 (Morikis et al., 2002; Soulika et al., 2006).

Additional structural information about C3 has become available recently (Fredslund et al., 2006; Janssen et al., 2006; Janssen et al., 2005; Nishida et al., 2006; Wiesmann et al., 2006). C3 (NCBI Protein Data Bank (PDB) Accession No. 2A73) is a two-chain molecule consisting of a β chain (res. 1-643; Ref. No. 2A73-A; SEQ ID NO:3) and an α-chain (res. 650-1,641) of 75 and 110 kDa respectively that are arranged in thirteen domains, whereas C3c (NCBI PDB Accession No. 2A74) consists of three chains: the β-chain (Ref. No. 2A74-A; SEQ ID NO:4) and two fragments of the α-chain, which form ten domains (Janssen et al., 2005). Activation of C3 occurs by cleavage of the scissile bond Arg-726-Ser-727, generating C3a (9 kDa) and C3b (176 kDa) (Bokisch et al., 1969). The transformation of C3 into C3b induces large conformational changes in the α-chain (Janssen et al., 2006; Wiesmann et al., 2006). In contrast, the β-chain is overall structurally stable. The only exception is the third macroglobulin (MG3) domains, which is part of the MG-ring of the β-chain and shows a reorientation up to 15° when changing from C3 to C3b and C3c (Janssen et al., 2006; Janssen et al., 2005; Wiesmann et al., 2006). The 40 kDa C-terminal fragment, identified by Soulika (Soulika et al., 2006), forms part of MG3 and complete MG4, MG5, $MG6^\beta$ and the linker (LNK) domain (Janssen et al., 2005). Thus, compstatin likely binds to the structurally stable part of C3.

As described above, the solution structure of compstatin, combined with experimental determinations of biological effect, have led to the development of analogs with improved complement inhibiting activity. However, a preferred situation in rational drug design is to have knowledge of the target protein structure along with bound ligands. The more available knowledge, the better the chances of designing and optimizing ligands to modulate therapeutic targets. Accordingly, the elucidation of the structure of compstatin bound to C3 is needed to facilitate rational drug design and to design pharmacophores and identify molecules with even greater activity and desirable biological features. The present invention satisfies this need.

SUMMARY OF THE INVENTION

One aspect of the invention features a complex of C3 (e.g., SEQ ID NO: 3) or C3c (e.g., SEQ ID NO:4) and compstatin (e.g., SEQ ID NO: 1 or 2), in crystalline form. In the complex, the compstatin is bound between domains MG4 and MG5 of the C3 or C3c. In particular, the β-sheets of MG4 and MG5 form a shallow groove in which the compstatin is bound. The compstatin in the complex comprises a β-turn formed by residues 8-11. In an exemplary embodiment, the compstatin comprises a three-dimensional configuration as depicted in FIG. 1D.

In one embodiment, residues Val-3, Trp-4 and Trp-7 of the compstatin (SEQ ID NO: 1) are involved in hydrophobic interactions with the β chain of C3 or C3c SEQ ID NO: 3 or SEQ ID NO:4) in the complex. The Trp-4 is also involved in CH/π and sulfur-aromatic interactions with residue Cys-12 of the compstatin. In particular embodiments, the complex comprises one or more hydrogen bond interactions between the compstatin and the C3c set forth in Table 2A. In additional embodiments, the complex comprises one or more hydrogen bond interactions within the compstatin set forth in Table 2B. In other embodiments, the complex comprises one or more hydrophobic interactions between the compstatin and the C3c set forth in Table 2C.

Another aspect of the invention features a computer readable medium comprising a data storage material encoded with machine readable data having stored thereon atomic coordinate/X-ray diffraction data defining a three-dimensional structure of a complex of C3 or C3c and compstatin in crystalline form, capable of displaying a three dimensional representation of the complex when read by an appropriate machine and processed by a computer program for determining molecule structures, wherein the data define at least the binding interactions between the compstatin and the C3 or C3c. Also featured is a computer comprising a processor in communication with a memory; the memory having stored therein the data as described above, and a program for generating the three-dimensional representation of the complex.

In one embodiment, the computer readable medium further comprises a pharmacophore model of compstatin that binds C3. The model is derived from the components of the atomic coordinate/X-ray diffraction data defining the three-dimensional structure of compstatin within the complex of C3 or C3c and compstatin in crystalline form. In a particular embodiment, the pharmacophore model of compstatin is derived from the data that define the binding interactions between the compstatin and the C3 or C3c.

Another aspect of the invention features a method for designing a complement inhibitor. The method comprises: (a) providing on a computer atomic coordinate/X-ray diffraction data defining a three-dimensional structure of a complex of C3c and compstatin in crystalline form; and (b) using a program operated by the computer to design a chemical compound predicted to bind to the C3c at the compstatin binding location and inhibit proteolytic activation of C3. In one embodiment, the designing step involves de novo rational drug design. In particular, the rational drug design can involve (i) identification of functional groups or small molecule fragments which can interact with sites in the binding location of compstatin on C3 or C3c, and (ii) linking the functional groups in a single compound. In certain embodiments, the designing step involves modifying the compstatin peptide structure.

In another embodiment, the designing step involves utilizing docking software and screening one or more databases for molecules that fit the compstatin binding location on C3.

In certain embodiments, the methods outlined above can further comprise: (c) synthesizing or obtaining the molecule that has been designed or identified; and (d) evaluating the molecule for its ability to perform one or more of (1) binding C3, (2) competing with compstatin for binding C3, (3) inhibiting proteolytic activation of C3, or (4) inhibiting complement activation.

Also featured in accordance with the invention is a molecule that binds C3 and inhibits complement activation, produced by the foregoing methods. The molecule can be a peptide or a partial peptide, or it can be a non-peptide chemical compound. In a preferred embodiment, the molecule inhibits complement activation at least as effectively as compstatin.

Other features and advantages of the invention will be understood by reference to the drawings, detailed description and examples that follow.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A, Ribbon representation of C3c (SEQ ID NO:4) with the bound compstatin peptide of SEQ ID NO: 1 in surface representation (between MG4 and MG5) C3c domains are distinguished by labeling and by color, when the drawing is presented in color. Also indicated are the anchor region (grey) and α'NT (black). FIG. 1B, Electron density ($2mF_{obs}-DF_{calc}$, $\phi_{calc}$) at 1σ of bound compstatin. FIG. 1C, Compstatin-C3c interaction site with C3c in surface representation (black residue numbering) and compstatin in stick representation (white residue numbering). When the drawing is viewed in color, the colors are according to FIG. 1A. FIG. 1D, Bound compstatin in stick representation (upper panel) and in ribbon representation (lower panel) with the disulfide bond indicated. FIG. 1E, Free compstatin (original peptide (Morikis et al., 1998)) shown in the same orientation and views as bound compstatin in FIG. 1D. Bound compstatin undergoes a conformational change upon binding to C3c. FIG. 1F, Stereo diagram of the superposition of the two compstatin molecules in the asymmetric unit shown in stick representation.

FIG. 2A, Residues involved in van der Waals contact, observed in both complexes within the asymmetric unit of the crystal, are shown in stick representation. FIG. 2B, Hydrogen bonds between C3c and compstatin and within compstatin itself, observed in both complexes within the asymmetric unit, are shown by yellow dotted lines (seen as grey in black-and-white version of the drawing). See Table 1 for all observed contacts between C3c and compstatin.

FIG. 3A, Ribbon representation of the compstatin binding site with C3c-compstatin (grey) C3c (cyan when the drawing is viewed in color) (Janssen et al., 2005) and C3 (green when the drawing is viewed in color) (Janssen et al., 2005) superposed using domain MG4 and MG5 (CCP4, 1994). Compstatin is omitted for clarity. Residues involved in compstatin binding are shown in stick representation and are numbered. In the compstatin binding site, free C3 resembles the C3c-compstatin complex more than free C3c. FIG. 3B, C3c-compstatin superposed onto C3 on the basis of MG1, MG2, MG4-MG6 of the β-ring (CCP4, 1994). C3c (grey) and C3 (β-chain, green and α-chain purple the latter two colors apparent when the drawing is viewed in color) are shown in ribbon representation, compstatin (wheat when the drawing is viewed in color) is shown in surface representation. The MG4-MG5 domain orientation is conserved between C3c-compstatin and C3; therefore compstatin binds C3 without affecting large structural changes.

FIG. 4A, Two symmetry related molecules of C3b contact each other at the compstatin binding site in the crystal of C3b (Janssen et al., 2006). Compstatin (circled) is superposed onto a C3b molecule (surface representation) on the basis of the C3c-compstatin structure. The symmetry related C3b molecule (ribbon representation) clashes severely with compstatin. FIG. 4B, Top diagram, cartoon representation of the back-to-back binding of C3 to the convertase (based on crystal structures of C3 (Janssen et al., 2005), C3b (Janssen et al., 2006; Wiesmann et al., 2006) and factor Bb (Ponnuraj et al., 2004)). Bottom diagram, cartoon representation of steric hindrance of C3 binding to the convertase induced by compstatin.

DETAILED DESCRIPTION OF ILLUSTRATIVE EMBODIMENTS

Undesired complement activation is a major cause of tissue injury in various pathological conditions and contributes to several immune complex diseases. Compstatin, a 13-residue peptide (e.g., SEQ ID NO: 1 or 2), is an effective inhibitor of C3 activation thus preventing a central and crucial step in complement activation. The precise binding site on C3, the structure in the bound form and the exact mode of action of compstatin heretofore were unknown. Presented in accordance with this invention is the crystal structure of compstatin in complex with C3c, a major proteolytic fragment of C3. Other aspects of the invention feature tools and methods of utilizing this information for identification and/or rational design of complement inhibitors.

Compstatin-C3c Crystal Structure

The crystal structure of compstatin in complex with C3c was determined to 2.4-Å resolution. Additional details of the structural determination are set forth in Example 1 herein. The resulting structure of the C3c-compstatin complex reveals an unexpected binding site and an unexpected conformation of compstatin. Nonetheless, the structure is in agreement with prior observations on the activity of compstatin and its derivatives; and, explains the species specificity. The available structural data identifies a model for the inhibitory activity of compstatin in blocking substrate C3 binding to C3 convertases.

Compstatin Binding to C3.

The crystal structure of the C3c-compstatin complex reveals that compstatin binds C3c between domains MG4 and MG5 of the β-chain. Compstatin undergoes a large conformational change upon binding to C3c. In contrast, C3c does not undergo large changes upon complex formation. The conformation of the compstatin binding site in C3c is structurally very similar to that observed in the structure of uncomplexed C3.

The observed compstatin-binding site is supported by biochemical data. Recently, the compstatin binding site was found to reside on the 40-kDa C-terminal region of the β-chain of C3 (Soulika et al., 2006). Both domains MG4 and MG5 are part of this region. Compstatin displays species specificity, it binds only to primate C3 and not to C3 from lower mammalian species (Sahu et al., 2003). The inventors have now demonstrated that residues Gly-345, His-392, Pro-393, Leu-454 and Arg-459 are all extensively involved in interactions with compstatin, as determined by the crystal structure set forth herein. These residues are conserved in primate C3, whereas they all differ in other mammals. These different amino-acid residues would yield steric hindrance or lead to loss of specific interactions; and, thus explain the species specificity observed for compstatin.

The structure of compstatin in the C3c-compstatin complex differs markedly from the structure of compstatin in solution, but corroborates previous activity data from mutational and other studies (Morikis et al., 1998 and 2002; Sahu et al., 2000 and 2003; Soulika et al., 2003; Katragadda et al., 2006). In the crystal structure, both main-chain and side-chain atoms contribute to the compstatin-C3c interactions, residues 2 and 3 of the hydrophobic cluster are involved in hydrophobic interaction with C3c, Val-3 and Trp-7 have extensive hydrophobic interactions with C3c; and, the amide indole of Trp-7 forms a hydrogen bond with the main-chain oxygen of Met-457 (see also Table 2 in Example 1), whereas the amide indole of Trp-4 does not form a hydrogen bond with C3c.

Figure 3:
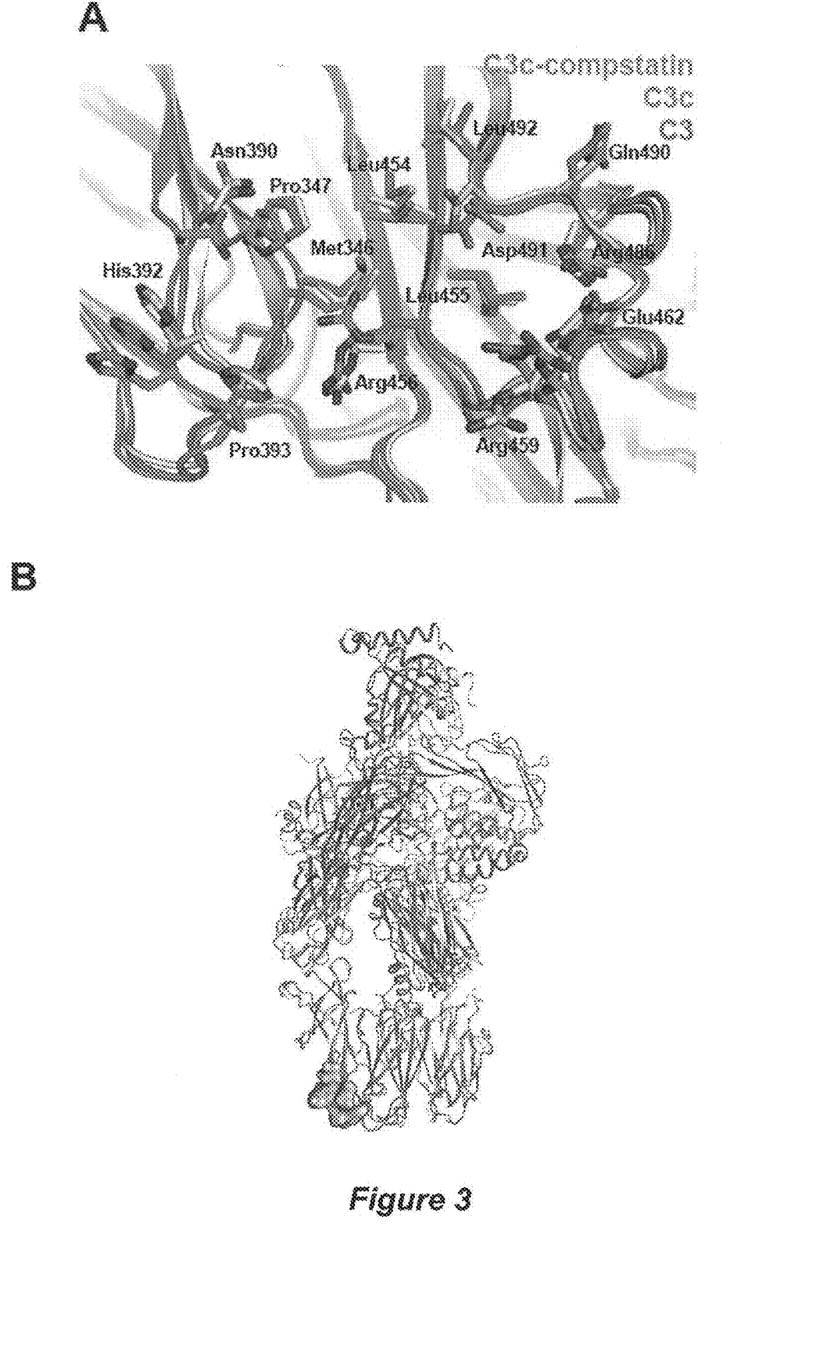
FIG. 3. Comparison of C3c-compstatin, C3c and C3.

Isothermal titration calorimetry experiments indicated that the C3-compstatin binding is an enthalpy driven process (Katragadda et al., 2004). It was proposed that the unfavorable entropy could arise from binding water molecules at the interface or could be due to conformational changes in C3 and/or compstatin (Katragadda et al., 2004). As described in the Examples herein, large structural differences were observed between free and bound compstatin. In contrast, only small structural differences are observed in the compstatin binding site region between structures of C3, C3c (Janssen et al., 2005) and C3c-compstatin (see also FIG. 3). Very few water molecules mediate the interactions between compstatin and C3c; this fits with the tight packing and the amount of hydrophobic interactions observed in the complex. Therefore, without being limited by any explanation of mechanism, it appears that the observed unfavorable entropy of complex formation arises mostly from the conformational change that compstatin undergoes upon binding to C3.

Compstatin's Mode of Action.

Two possible mechanisms for complement inhibition by compstatin have been proposed: compstatin either (i) sterically hinders binding of C3 to the convertase or (ii) induces conformational changes in C3 preventing binding of C3 to the convertase. The structural data set forth herein clearly show that the binding site of compstatin lies far away from any other known binding site on C3 or its proteolytic fragments (Janssen and Gros, 2007), and that compstatin binds C3 without causing large structural changes. These data are consistent with the observation that compstatin does not interfere with the formation of the C3 convertase or with the function of any of the complement regulatory proteins (Sahu et al., 1996). In addition, binding of compstatin to C3 does not increase protease sensitivity (Sahu et al., 1996); in contrast to bacterial protein Efb-C, which affects protease sensitivity by changing the conformation of C3 (Hammel et al., 2007). The effect observed by isothermal titration calorimetry (ITC) and surface plasmon resonance (SPR) suggested that conformational changes play an important role in compstatin-C3 binding (Katragadda et al., 2004; Sahu et al., 2000). However, the marked conformational change of compstatin observed herein suffices to explain the SPR and ITC results. It is therefore concluded that compstatin does not act by changing the conformation of C3, but likely acts through sterically hindering the binding of C3 to the convertase.

Figure 4:
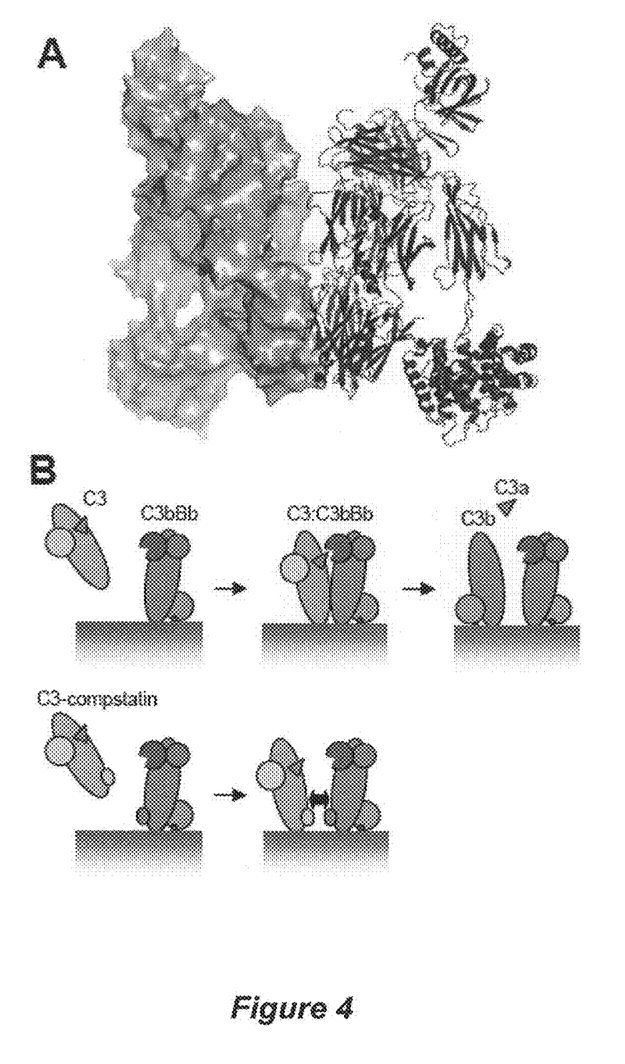
FIG. 4. Model for inhibition by compstatin.

How does compstatin sterically hinder C3 binding to the convertases? Most binding sites for interacting proteins have been mapped to the α-chain of C3 (Janssen and Gros, 2007). The exception is the recently identified complement receptor CRIg, which also inhibits convertase activity (Wiesmann et al., 2006). Crystal structures revealed that CRIg binds C3b and C3c predominantly at domains MG3 and MG6 of the β-chain (Wiesmann et al., 2006). Compstatin binds C3 between domains MG4 and MG5. These two binding sites of CRIg and compstatin are >20 Å apart, but lie on the same face of the MG-ring of the β-chain. Notably, in the crystal of C3b, a C3b-C3b binding site is formed by the same face of the MG-ring (see FIG. 4A) (Janssen et al., 2006). This MG-ring interaction face may indicate a major exosite in substrate binding forming the C3:C3bBb substrate:enzyme complex. Both CRIg and compstatin would sterically hinder the formation of this interface of the substrate:enzyme complex, and hence explain the inhibitory activity of both molecules (see also FIG. 4B). Compstatin may also bind the enzyme complex, C3bBb (Sahu et al., 1996). In the back-to-back model of the MG-ring interaction in C3:C3bBb substrate:enzyme complex, compstatin might inhibit the interaction both ways; either through binding the substrate or through binding the enzyme complex. This additional mechanism may explain the higher inhibitory activity of compstatin in the alternative pathway (AP) compared to the classical pathway (CP) (Furlong et al., 2000; Sahu et al., 1996). In the CP, compstatin can only bind to C3 and not to the convertase C4bC2a (Sahu et al., 2003), whereas in the AP, compstatin can bind both the substrate C3 and the convertase C3bBb thus possibly acting in a dual way. Thus, based on an interaction surface observed in C3b crystals and the interaction sites of compstatin and CRIg a model for C3 binding to the convertase has been formed. This model explains how a small peptide inhibitor, compstatin has the same inhibitory effect as the large protein receptor CRIg.

In sum, the inventors have identified that the potential therapeutic compstatin binds C3 on a shallow groove between two domains of the β-chain. Most drug design projects target well-defined pockets in proteins for binding low molecular weight inhibitors to achieve high binding affinity and specificity. Remarkably, compstatin binds on a rather flat surface of the C3c molecule. Nevertheless, it has been possible to improve the specific activity by structure-activity studies and experimental and theoretical combinatorial approaches (reviewed by Morikis et al., 2004). The structure of the complex between C3c and compstatin provides crucial information on the bound conformation of compstatin and the binding site on C3. These data provide new tools to develop improved and less costly non-peptide inhibitors, for example by developing or identifying molecules that structurally mimic the bound form of compstatin. Further, the detailed knowledge of the binding site provides the possibility to develop a mouse model by conservatively "humanizing" mouse C3 to enable in vivo testing of complement inhibition of compstatin and derivatives in various complement disease models. Finally, the current data indicate a potential role for the large MG-ring of the β-ring in substrate binding to the convertase.

Tools and Methods

The determination of the three-dimensional structure of the compstatin-C3c complex as described herein enables the identification and/or design of compstatin analogs or new agents that emulate and improve upon the complement-inhibiting activity of compstatin, preferably while introducing advantageous new pharmaceutical characteristics. An initial step is to use the structural information in a computational program to design a pharmacophore defining the interaction of compstatin with C3. As used herein, the term "pharmacophore" refers to the spatial orientation of various functional groups or features necessary for activity at a biomolecular target. The pharmacophore preferably includes surface-accessible features of the individual binding partners (in this instance, compstatin or C3) and/or at the interface between the binding partners, such as hydrogen bond donors and acceptors, charged groups or hydrophobic sites as described herein. Such features may be included in a pharmacophore model based on their relative importance to the biological activity.

Pharmacophores are typically determined by inputting the available atomic coordinates and other structural information into a computer-readable medium and utilizing appropriate computer software to generate a model, or by using manual modeling based on known conformation of lead compounds (e.g., compstatin). The pharmacophore may be used for de novo rational drug design, and/or to screen in silico compound libraries, using available computer software, as described in more detail below.

In one embodiment, molecular modeling techniques are used for de novo design of compounds. The molecular modeling steps utilize the structural information obtained from crystals of compstatin-C3c according to the present invention. In one embodiment, the de novo drug design involves the identification of functional groups or small molecule fragments that can interact with the binding surface of human C3 and exert a complement-inhibiting biological effect, and linking these groups or fragments into a single compound. Once such functional groups are identified, they can be linked into a single compound using bridging components having suitable size and geometry to fit the compstatin binding site on C3 and exert the biological effect. Computer programs for designing geometrically appropriate links and bridges for functional groups are known in the art and are preferred over manual techniques for use in the present invention. Such software includes programs or suites of programs such as QUANTA or SYBYL. Other software, e.g., HOOK (Eisen, MB et al, 1994), which links multiple functional groups with molecular templates from a database, and CAVEAT (Lauri and Bartlett, 1994), for designing linking units to constrained acyclic molecules, is also available.

In a preferred embodiment of the invention, pharmacophores determined by the structural information provided herein are utilized for in silico screening of compound libraries. Several docking and computational screening methods and drug design tools are particularly suitable to identify complement inhibitors using the structural information provided in accordance with the invention. For instance, well-tested docking software such as LUDI, AUTODOCK and AFFINITY may be used for flexible docking of a peptide analog, peptidomimetic or other pharmacophore onto the interaction surface of the above-selected complement proteins.

LUDI (Böhm, 1992) is a powerful computational tool for structure based rational drug design. LUDI fits molecules into the active site of a receptor by matching complementary polar and hydrophobic groups. An empirical scoring function is used to prioritize the hits. LUDI can also suggest modifications that may increase the binding affinity between an existing ligand and the receptor. If the receptor structure is not known, LUDI can suggest a ligand candidate by inference from a set of active analogs. LUDI/CAP enables the design tools of LUDI to select commercially-available chemical fragments based on the "Chemicals Available for Purchase" (CAP) and CAP Screening databases of Accelrys, Inc. (San Diego, Calif.) LUDI/CAP provides access to over 65,000 commercially available structures to accelerate searches for drug candidates.

AUTODOCK (Morris et al., 1998) is a suite of automated docking tools. It is designed to predict how small molecules, such as substrates or drug candidates, bind to a receptor of known 3-dimensional structure, as is now known for the binding location of compstatin on C3. The procedure uses a Monte Carlo (MC) and simulated annealing (SA) technique for configurational exploration with a rapid energy evaluation using grid-based molecular affinity potentials. It thus combines the advantages of exploring a large search space and a robust energy evaluation to the problem of docking a flexible substrate into the binding site of a static protein. Input into to the procedure is minimal. The researcher specifies a rectangular volume around the protein, the rotatable bonds for the substrate, and an arbitrary or random starting configuration, and the procedure produces a relatively unbiased docking.

AFFINITY is a module of INSIGHT-II software from Accelrys, Inc. (San Diego, Calif.) that automatically docks ligands to receptors identifying low energy orientations of the ligand within the receptor. For a given assembly consisting of a ligand molecule and a receptor molecule, AFFINITY uses force field based methods to automatically find the best binding modes of the ligand to the receptor. This energy-driven method is especially useful in structure-based drug design where the experimentally determined structure of a protein-ligand complex is often unavailable. Many cases have been observed where ligand binding is accompanied by some level of conformational change in the protein receptor. These changes range from side chain movements to displacements of whole loop regions. AFFINITY allows exploration of these potential movements by defining flexible areas in the protein receptor binding site as well as in the ligand. AFFINITY uses a two-step process to dock the ligands. First, initial placement of the ligand within the receptor is made using an MC-type procedure to search both conformational and Cartesian space. Second, a simulated annealing phase optimizes the location of each ligand placement. During this phase, AFFINITY holds the "bulk" of the receptor (defined as atoms not in the user-specified binding site) rigid, while the binding site atoms and ligand atoms are movable. In its treatment of nonbonded interactions, AFFINITY allows the use of grid-based method. Interactions between the bulk (non-flexible) and movable atoms are approximated by the very accurate and efficient molecular mechanical/grid (MM/Grid) method developed by Luty et al. (1995) while interactions among movable atoms are treated using a full force field representation. Solvation effects are included using the methods of Stouten et al. (1993).

Recently, a method was devised for predicting protein binding sites using sequence conservation and covariation information (Dunn et al., 2005; Vicatos et al., 2005). It was demonstrated that the accuracy of widely used binding site prediction algorithms improves significantly with bioinformatics methods. Based on the observation that the density of conserved residue positions is higher at the interface regions of interacting protein surfaces we compute conservation indices of residue positions on the surfaces of interacting use this information to score patches on the surface of protein the binding sites on the surfaces of C3 and C5 molecules. With a list of candidate binding sites, the tools described above are used to dock PubChem compounds and identify potential inhibitors.

The novelty of this approach is the leveraging of the PubChem and TeraGrid resources, harnessing an unprecedented amount of computational assets. Indeed, a major shortcoming of protein-ligand simulations is the computational resources required. An average of 0.1 h of CPU is required for each compound on a 1.5-GHz Intel-PentiumIV LINUX-based PC. Although the overall cost for simulated compounds in small datasets is negligible, this method was not readily amenable for high-throughput computational screening of hundreds of thousands of drug-like molecules, before the advent of the TeraGrid.

The TeraGrid is the highest-end resource currently available. It reflects the idea of harnessing and using distributed computers, data storage systems, networks, and other resources as if they were a single massive system, employing software technologies to allow researchers to create "virtual supercomputers" far larger than individual hardware components. The TeraGrid software is based on commodity clusters, Linux/Unix, and Globus hardware. Currently the TeraGrid provides more than 40 Teraflops of computing power, distributed at multiple sites, facilities and personnel for storing and managing more than one Petabyte of data, high-resolution visualization environments and toolkits for Grid computing, all connected with a 40 gigabit-per-second network (see www address teragrid.org). It is worth noting that the roadmap of the Extensible Terascale Facilities explicitly states the vision for continually increasing the horsepower of the TeraGrid to one Petaflop over the next five years. With thousands of computers potentially available, simulating millions of compounds in a few days is now indeed feasible. This creates the opportunity for conducting docking simulations with sufficient accuracy to enable effective virtual screening of hundreds of thousands of compounds. High scoring compounds predicted from this analysis are obtained and tested for their complement-inhibiting activities.

The complement activation-inhibiting activity of compstatin mimetics, pharmacophores and other such compounds identified or produced in accordance with the foregoing methods may be tested by a variety of assays known in the art. In a preferred embodiment, the assay described in Example 2 is utilized. A non-exhaustive list of other assays is set forth in U.S. Pat. No. 6,319,897, including, but not limited to, (1) peptide binding to C3 and C3 fragments; (2) various hemolytic assays; (3) measurement of C3 convertase-mediated cleavage of C3; and (4) measurement of Factor B cleavage by Factor D.

The following examples are provided to describe the invention in greater detail. They are intended to illustrate, not to limit, the invention.

Example 1

This example describes determination of the crystal structure of compstatin in complex with C3c to 2.4-Å resolution. C3c was used instead of C3 because C3c crystallizes more readily than C3 and crystals of C3c diffract to a higher resolution than those of C3.

Methods

Protein Purification and Peptide Synthesis.

C3c was purified as described previously (Janssen et al., 2005). In brief, C3c (*NCBI Protein Data Bank Ref. No.* 2A74; the β chain having SEQ ID NO:4) from outdated human plasma (stored for several weeks at 4° C.) was purified by polyethylene glycol (PEG) precipitation, anion-exchange chromatography (DEAE Sephacel), cation-exchange chromatography (CM-Sephadex C50) and size-exclusion chromatography (Sephacryl 300). C3c was concentrated to 20 mg ml$^{-1}$ and dialyzed against 10 mM Tris pH 7.4, 2 mM EDTA and 2 mM benzamidine. The glycan moiety on Asn917 was cleaved off with N-Glycosidase F (PNGase F). The improved compstatin analogue (Ac-ICVWQDWGAHRCT-NH$_2$; SEQ ID NO: 1) displaying 45-fold higher activity compared to the parent peptide was synthesized and purified as described previously (Mallik et al., 2005). Prior to crystallization C3c at 20 mg/ml (0.148 mM) in 10 mM Tris pH 7.4, 2 mM EDTA, and 2 mM benzamidine was mixed with lyophilized compstatin to a final concentration of 4.8 mg/ml (3.0 mM).

Crystallization and Data Collection.

C3c-compstatin was crystallized in hanging drops from mother liquor containing 18% w/v PEG-monometylether 2000, 200 mM potassium bromide and 100 mM Tris pH 7.0 at 20° C. Crystals grew up to 250×200×200 µm within 2 weeks. For cryo-protection crystal were briefly transferred to 8% v/v 2,3 butanediol, 18% w/v PEG-monometylether 2000, 500 mM potassium bromide, 100 mM Tris pH 7.0. and flash-cooled in liquid nitrogen. Crystals displayed space group $P2_1$ (a=85.8, b=124.7, c=127.4 Å, β=95.1°, contained two molecules per asymetric unit and diffracted to 2.4-Å resolution at ESRF beamline ID23-1. Diffraction data was processed using MOSFLM/CCP4 (CCP4, 1994) (data statistics are presented in Table 3)

Structure Determination.

C3c-compstatin was solved by molecular replacement with Phaser (McCoy et al., 2005). First C3c (pdb code 2A74) (Janssen et al., 2005) without the C345c domain was placed. Second the C345c domain of C3c was placed using Coot (Emsley and Cowtan, 2004) and its position was refined by Phaser. Subsequently all domains were refined by rigid-body refinement in Phaser. Compstatin and C3c were finalized by several rounds of model building in Coot and refinement in REFMAC (CCP4, 1994) to R and $R_{free}$ values of 21.3% and 28.1% (see also FIG. 1B and Table 3). The final refined model contained 1107 residues for C3c molecule 1 (chains A, B and C) and 1113 residues for C3c molecule 2 (chains D, E and F). Both compstatin molecules were completely built. All molecular graphics figures were generated with pymol (W. Delano; worldwide web—pymol.org/).

Results

Structure of the C3c-Compstatin Complex.

Presented herein is the structure of compstatin in complex with C3c. C3c was co-crystallized with the Ac-V4W/H9A-NH₂ analogue (Ac-ICVWQDWGAHRCT-NH₂) (SEQ ID NO:1) of compstatin (Mallik et al., 2005); hereafter referred to as compstatin. Crystals diffracted to 2.4-Å resolution and displayed space group $P2_1$. Two complexes of C3c-compstatin are present in the asymmetric unit. Complex formation agrees with the 1:1 stoichiometry determined by surface-plasmon resonance (Sahu et al., 2000). The overall structures of the independent C3c-compstatin complexes are very similar. Differences are observed in the orientation of some domains (see Table 1a, 1b).

The differences, which are the largest for C345c, MG8, MG7 and MG3 (in decreasing order), correspond with observed variations for these domain in other structures of C3 and its fragments (Janssen et al., 2006; Janssen et al., 2005; Wiesmann et al., 2006).

TABLE 1a

Domain rotation and translation between the two C3c-compstatin complexes in the asu

| Chains A, B, C, G - chains D, E, F, H | translation (Å) | rotation (°) |
|---|---|---|
| MG1 | 0.4 | 3.1 |
| MG2 | 0.7 | 3.5 |
| MG3 | 1.5 | 4.4 |
| MG4 | 0.5 | 2.4 |
| MG5 | 0.2 | 0.5 |
| MG6 | 0.7 | 4.5 |
| LNK | 0.1 | 1.0 |
| MG7 | 2.0 | 5.3 |
| MG8 | 3.5 | 7.1 |
| C345C | 5.3 | 7.2 |
| Compstatin | 0.4 | 1.1 |

TABEL 1b

Domain rotation and translation between the two C3c-compstatin complexes and two C3c molecules

| C3c-compstatin - C3c | mol. 1 on 1 | | mol. 1 on 2 | | mol. 2 on 1 | | mol. 2 on 2 | |
|---|---|---|---|---|---|---|---|---|
| | translation (Å) | rotation (°) | translation (Å) | rotation (°) | translation (Å) | rotation (°) | translation (Å) | rotation (°) |
| MG1 | 0.7 | 3.5 | 0.3 | 2.0 | 0.4 | 1.3 | 0.5 | 3.2 |
| MG2 | 0.5 | 2.8 | 0.2 | 1.2 | 0.5 | 4.3 | 0.5 | 2.6 |
| MG3 | 1.2 | 3.6 | 0.4 | 0.7 | 0.5 | 0.8 | 1.1 | 4.1 |
| MG4 | 0.6 | 3.6 | 0.3 | 2.4 | 0.4 | 3.3 | 0.3 | 3.0 |
| MG5 | 0.2 | 1.9 | 0.2 | 1.9 | 0.0 | 1.4 | 0.2 | 1.7 |
| MG6 | 0.8 | 5.6 | 0.3 | 3.7 | 0.2 | 0.6 | 0.5 | 4.1 |
| LNK | 0.7 | 0.6 | 0.0 | 0.6 | 0.2 | 0.3 | 0.1 | 1.6 |
| MG7 | 1.5 | 3.1 | 0.7 | 2.4 | 0.8 | 2.4 | 1.4 | 3.0 |
| MG8 | 1.5 | 1.7 | 0.9 | 1.6 | 2.0 | 8.3 | 2.6 | 5.7 |
| C345C | 4.2 | 15.4 | 3.0 | 12.7 | 5.1 | 12.5 | 5.5 | 12.1 |

Figure 1:
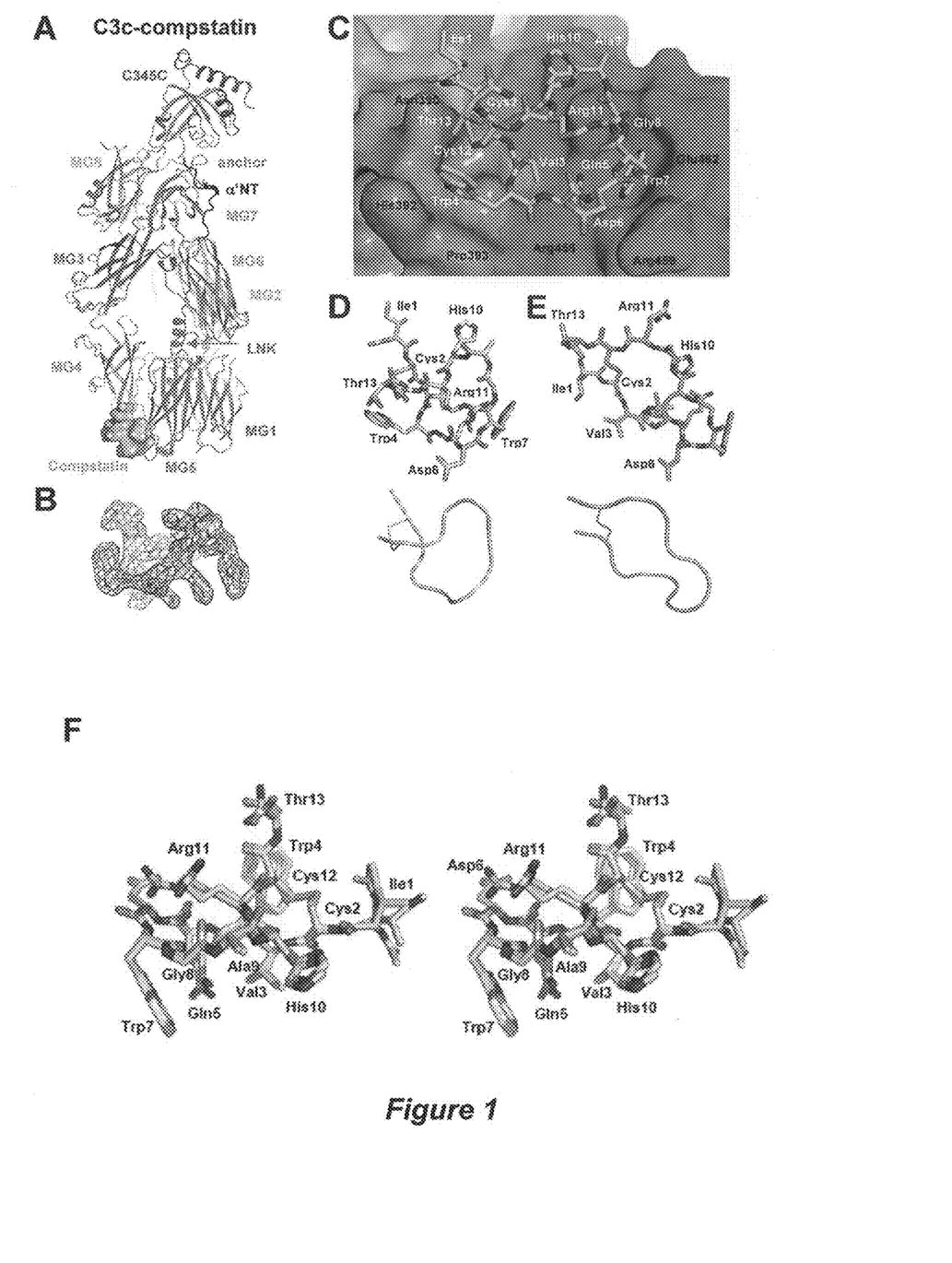
FIG. 1. Structure of the C3c-compstatin complex at 2.4-Å resolution.

The structure of the C3c-compstatin complex reveals that compstatin binds between domains MG4 and MG5 (FIG. 1). The MG4 and MG5 domains are part of the 40 kDa C-terminal fragment of the β-chain; thus, the observed binding site is in agreement with prior biochemical data (Soulika et al., 2006). The β-sheets (consisting of strands βA, βB and βE) of MG4 and of MG5 form a shallow groove. Compstatin binds to the lower end of this groove. Thus, compstatin binds C3c at the bottom end of the MG-ring, far away from the α-chain.

Structure of Compstatin.

Compstatin bound to C3c differs markedly in conformation from that of free compstatin (Morikis et al., 1998) (see FIG. 1D, 1E). In complex with C3c, compstatin is folded in a conformation with a β-turn formed by residues 8-11. The N- and C-termini point outwards and are outside of the main loop formed by residues 2-10, which is covalently closed by the disulphide bond between Cys-2 and Cys-12. Between the two complexes in the asymmetric unit, compstatin differs only in the orientation of Ile-1 and the acetylated N-terminus and Arg-11 (FIG. 1F). This conformation of compstatin differs from those present in the NMR ensemble of free compstatin (Mallik et al., 2005; Morikis et al., 1998). Free compstatin has a β-turn at residues 5-8, whereas in bound compstatin a β-turn at residues 8-11 is observed. The side-chain interactions between residues 3, 4 and 7 required for conformational stability of free compstatin (Morikis et al., 1998) are absent in bound compstatin. In contrast, residues Val-3, Trp-4 and Trp-7 are involved in hydrophobic interactions with C3c in bound compstatin. Furthermore, Trp-4 and Trp-7 in bound compstatin do not show π-π stacking interactions (Mallik et al., 2005), instead Trp-4 is involved in CH/π and sulphur-aromatic interactions with Cys-12 when bound to C3c. These data show clearly that compstatin undergoes a dramatic conformational rearrangement upon binding to C3c.

Structure of C3c.

The structure of C3c in complex with compstatin reveals the same overall domain arrangement of 10 domains as observed for free C3c (Janssen et al., 2005). For most domains we observe small variations in domain orientation among the two structures of C3c-compstatin and the two structures of free C3c in the asymmetric unit (see Table 1b). Large differences are observed for C345c (up to 15.4° rotation) and MG8 (up to 8.3° rotation). These differences reflect the flexibility of the C3c molecule. Differences in domain orientation of MG4 and MG5 within C3c range from 2.4 to 3.6° and 1.4 to 1.9° respectively. The relative orientations between MG4 and MG5 differ by only 4.2° among these structures of C3c. These data indicate that compstatin does not affect the overall domain arrangement of C3c.

Compstatin-C3c Interactions.

Figure 2:
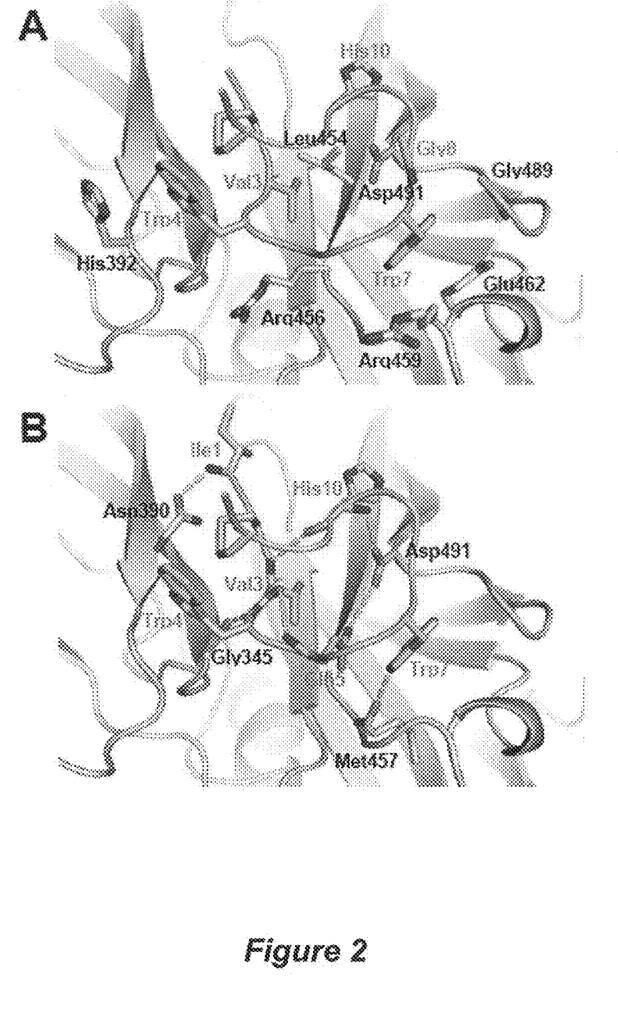
FIG. 2. Interactions between C3c and compstatin, and sequence alignments. C3c colored grey and compstatin colored as in FIG. 1A when the drawing is viewed in color.

Compstatin interacts extensively with C3c. One side of the compstatin-loop structure faces C3c and one side faces the solvent with residues 2-9 alternating inside and outside. Residues 11-13 extend outward away from C3c. In total 40% of the molecular surface of compstatin is buried in the complex, resulting in 1,120 Å$^2$ buried surface area of the complex. The interface of compstatin with C3c is characterized by both hydrophobic and hydrophilic interactions (see Table 2). Notably, Val-3 and the Trp-7 of compstatin are buried in hydrophobic pockets formed by C3c residues Met-346, Pro-347, Leu-454, Arg-456 and Leu-455, Arg-456, Arg-459, Glu-462 respectively (FIGS. 1C and 2A). A hydrogen bonding network between both backbone and side-chain atoms of C3c and compstatin further stabilize the interaction (Table 2a and FIG. 2B). A small difference in bound waters is observed in the interface of compstatin with C3c between the two complexes in the asymmetric unit. In one complex (chains A, B and C for C3c and chain G for compstatin in the deposited pdb file) we observe no bound water molecule, whereas in the other complex (chains D, E and F and chain H respectively) we observe two water molecules mediating hydrogen bonding between compstatin and C3c. The water molecules mediate interactions between compstatin Gln-5 and C3c Asp-491 and the backbone carbonyl oxygens of compstatin Cys-2 and C3c Thr-391. This small difference in bound waters possibly reflects flexibility and small differences in crystal packing. Alternatively, we possibly have not observed all bound water molecules due to the limited resolution of 2.4 Å. For both complexes we observe a bromide ion bound in the interface. This ion forms hydrogen bonds with the backbone nitrogen of compstatin Asp-6 and backbone nitrogen of C3c Arg-459. The crystallization solution contained 200 mM KBr, whereas the cryo-protectant contained 500 mM KBr. Possibly, the stabilizing role of bromide is replaced by a water molecule in conditions without bromide present.

TABLE 2

Interactions between compstatin and C3c
Interactions were calculated with Ligplot (Wallace et al., 1995).
Distances are listed for both molecule 1 (chains A, B, C and G on the left) and molecule 2 (chains D, E, F and H on the right). Residue numbering 0-14 are from compstatin, residue numbering 345-492 are from C3c.

A: Hydrogen bonds between compstatin and C3c

| Donor | | Acceptor | | Distance (Å) | |
|---|---|---|---|---|---|
| Ace0 | O | Asn390 | OD1 | | 2.95 |
| Ile1 | N | Asn390 | OD1 | 2.88 | 2.54 |
| Trp4 | N | Gly345 | O | 3.05 | 2.98 |
| Gln5 | NE2 | Leu455 | O | | 2.66 |
| Gln5 | NE2 | Asp491 | OD2 | 2.72 | 3.26 |
| Trp7 | NE1 | Met457 | O | 2.63 | 2.57 |
| His10 | N | Asp491 | OD1 | 2.81 | 2.61 |
| Arg456 | NE | Trp4 | O | | 3.06 |
| Met457 | N | Gln5 | OE1 | | 2.85 |

B: Hydrogen bonds within compstatin

| Donor | | Acceptor | | Distance (Å) | |
|---|---|---|---|---|---|
| Val3 | N | His10 | O | 3.02 | 2.99 |
| Gln5 | N | Val3 | O | 2.94 | 3.03 |
| Cys12 | N | Val3 | O | | 3.01 |
| Thr13 | OG1 | Cys12 | O | 2.95 | |
| NH$_2$14 | N | Cys12 | O | | 2.48 |

C: Hydrophobic interactions between C3c and compstatin

| Compstatin | | C3c | | Distance (Å) | |
|---|---|---|---|---|---|
| Cys2 | SG | Asn390 | CG | | 3.84 |
| Val3 | CG2 | Met346 | CE | 3.88 | |
| Val3 | CG2 | Pro347 | CD | 3.84 | |
| Val3 | CG2 | Leu454 | CD2 | 3.79 | 3.82 |
| Val3 | CG2 | Leu454 | CG | 3.70 | 3.81 |
| Val3 | CG1 | Arg456 | CB | 3.84 | 3.74 |
| Val3 | CG1 | Arg456 | CD | 3.46 | 3.90 |
| Trp4 | CB | Pro393 | CG | 3.59 | |
| Trp4 | CZ2 | His392 | CE1 | 3.71 | 3.68 |
| Gln5 | CD | Arg456 | CA | | 3.88 |
| Trp7 | CH2 | Leu455 | CD2 | 3.89 | |
| Trp7 | CD1 | Arg459 | CA | 3.70 | 3.79 |
| Trp7 | CD1 | Arg459 | CB | | 3.83 |
| Trp7 | CE2 | Glu462 | CG | | 3.81 |
| Trp7 | CE2 | Glu462 | CB | 3.85 | |
| Trp7 | CZ2 | Glu462 | CB | 3.66 | 3.66 |
| Trp7 | CZ3 | Gly489 | C | 3.56 | 3.71 |
| Gly8 | C | Asp491 | CG | 3.80 | |
| Gly8 | CA | Asp491 | CG | 3.50 | 3.68 |
| His10 | CD2 | Asp491 | CB | 3.86 | 3.43 |
| His10 | CD2 | Leu492 | CB | | 3.70 |

TABLE 3

Data collection and refinement statistics

Data collection

| | |
|---|---|
| Space group | P2$_1$ |
| Cell dimensions | |
| a, b, c (Å) | 85.8, 124.8, 127.4 |
| β (°) | 95.1 |
| Resolution (Å) | 33-2.4 (2.53-2.4)* |
| R$_{merge}$ (%) | 6.7 (43.5) |

TABLE 3-continued

Data collection and refinement statistics

| | |
|---|---|
| I/σI | 13.4 (2.4) |
| Completeness (%) | 96.4 (98.0) |
| Redundancy | 3.0 (2.9) |
| Refinement | |
| Resolution (Å) | 33-2.4 |
| No. reflections | 95439 |
| $R_{work}/R_{free}$ (%) | 21.3/28.1 |
| No. atoms | |
| C3c | 17638 |
| Compstatin | 226 |
| Water | 471 |
| Ligand/ion | 145 |
| Average B-factor (Å²) | |
| C3c | 46.2 |
| Compstatin | 47.0 |
| Water | 39.7 |
| Ligand/ion | 57.4 |
| R.m.s deviations | |
| Bond lengths (Å) | 0.011 |
| Bond angles (°) | 1.408 |

*Highest resolution shell is shown in parenthesis.

Comparison of C3c-Compstatin with C3.

Several structures of C3 and its fragments C3b and C3c are now available (Janssen et al., 2006; Janssen et al., 2005; Wiesmann et al., 2006). Comparison of the medium to high resolution structures of C3, C3c, C3c-CRIg and C3c-compstatin shows that the MG4-MG5 domain orientation is conserved (see also FIG. 3). Difference in orientations of other domains, notably C345c, MG8, MG7 and MG3, can be attributed to inherent flexibility of the molecule. However, we observe significant differences in the compstatin binding site. The loop βE-βF of MG4 and positions of amino-acid side chains differ up to 4.6 Å between C3c-compstatin and free C3c (see FIG. 3A). Surprisingly, the positions of the side chains in the C3c-compstatin complex resembles more free C3 than free C3c, see for example the positions of Asn-390, His-392 and Pro-393 of loop βE-βF, Pro 347 and Arg-456 in FIG. 3A. These differences between C3, C3c-compstatin and C3c may explain the higher affinity of compstatin for C3 ($K_d$ of 0.14 µM) than for C3c (Katragadda et al., 2004; Sahu et al., 2000). Overall, we may conclude that compstatin binding does not induce large rearrangements in C3c, but minor, local induced effects are present in the vicinity of the compstatin binding site.

Example 2

Inhibitory activity of compstatin or its analogs on the complement system was determined by measuring their effect on the activation of the complement system by immunocomplexes. Complement activation inhibition was assessed by measuring the inhibition of C3 fixation to ovalbumin-anti-ovalbumin complexes in normal human plasma. Microtiter wells were coated with 50 µl of ovalbumin (10 mg/ml) for 2 hr at 25° C. (overnight at 4° C.). The wells were saturated with 200 µl of 10 mg/ml BSA for 1 hr at 25° C. and then a rabbit anti-ovalbumin antibody was added to form an immunocomplex by which complement can be activated. Thirty microliters of peptides at various concentrations were added directly to each well followed by 30 µl of a 1:80 dilution of human plasma. After 30 min incubation, bound C3b/iC3b was detected using a goat anti-human C3 HRP-conjugated antibody. Color was developed by adding ABTS peroxidase substrate and optical density measured at 405 nm.

The absorbance data obtained at 405 nm were translated into % inhibition based on the absorbance corresponding to 100% complement activation. The % inhibition was plotted against the peptide concentration, and the resulting data set was fit to the logistic dose-response function using Origin 7.0 software. The concentration of the peptide causing 50% inhibition of C3b/iC3b deposition was taken as the $IC_{50}$ and used to compare the activities of various peptides. $IC_{50}$ values were obtained from the fitted parameters that achieved the lowest chi-square value.

REFERENCES

Bokisch, V. A., Muller-Eberhard, H. J. and Cochrane, C. G. (1969) Isolation of a fragment (C3a) of the third component of human complement containing anaphylatoxin and chemotactic activity and description of an anaphylatoxin inactivator of human serum. *J Exp Med*, 129, 1109-1130.

Böhm, H. J. (1992) The computer program LUDI: a new method for the de novo design of enzyme inhibitors. *J Comput Aided Mol Des.*, 6, 61-78.

Bureeva, S., Andia-Pravdivy, J. and Kaplun, A. (2005) Drug design using the example of the complement system inhibitors' development. *Drug Discov Today*, 10, 1535-1542.

Carroll, M. C. (2004) The complement system in regulation of adaptive immunity. *Nat Immunol*, 5, 981-986.

CCP4. (1994) The CCP4 suite: programs for protein crystallography. *Acta Crystallogr D Biol Crystallogr*, 50, 760-763.

Duan, Y., Reddy, B. V. and Kaznessis, Y. N. (2005) Physicochemical and residue conservation calculations to improve the ranking of protein-protein docking solutions. *Protein Sci.* 14, 316-328.

Eisen, M. B., Wiley, D. C., Karplus, M. and Hubbard, R. E (1994) HOOK: A program for finding novel molecular architectures that satisfy the chemical and steric requirements of a macromolecule binding site. *Proteins: Structure, Function, and Genetics*, 19, 199-221.

Emsley, P. and Cowtan, K. (2004) Coot: model-building tools for molecular graphics. *Acta Crystallogr D Biol Crystallogr*, 60, 2126-2132.

Fredslund, F., Jenner, L., Husted, L. B., Nyborg, J., Andersen, G. R. and Sottrup-Jensen, L. (2006) The structure of bovine complement component 3 reveals the basis for thioester function. *J Mol Biol*, 361, 115-127.

Furlong, S. T., Dutta, A. S., Coath, M. M., Gormley, J. J., Hubbs, S. J., Lloyd, D., Mauger, R. C., Strimpler, A. M., Sylvester, M. A., Scott, C. W. and Edwards, P. D. (2000) C3 activation is inhibited by analogs of compstatin but not by serine protease inhibitors or peptidyl alpha-ketoheterocycles. *Immunopharmacology*, 48, 199-212.

Hammel, M., Sfyroera, G., Ricklin, D., Magotti, P., Lambris, J. D. and Geisbrecht, B. V. (2007) A structural basis for complement inhibition by Staphylococcus aureus. *Nat Immunol*, 8, 430-437.

Holland, M. C., Morikis, D. and Lambris, J. D. (2004) Synthetic small-molecule complement inhibitors. *Curr Opin Investig Drugs*, 5, 1164-1173.

Janssen, B. J., Christodoulidou, A., McCarthy, A., Lambris, J. D. and Gros, P. (2006) Structure of C3b reveals conformational changes that underlie complement activity. *Nature*, 444, 213-216.

Janssen, B. J. and Gros, P. (2007) Structural insights into the central complement component C3. *Mol Immunol*, 44, 3-10.

Janssen, B. J., Huizing a, E. G., Raaijmakers, H. C., Roos, A., Daha, M. R., Nilsson-Ekdahl, K., Nilsson, B. and Gros, P. (2005) Structures of complement component C3 provide insights into the function and evolution of immunity. *Nature*, 437, 505-511.

Katragadda, M., Magotti, P., Sfyroera, G. and Lambris, J. D. (2006) Hydrophobic effect and hydrogen bonds account for the improved activity of a complement inhibitor, compstatin. *J Med Chem*, 49, 4616-4622.

Katragadda, M., Morikis, D. and Lambris, J. D. (2004) Thermodynamic studies on the interaction of the third complement component and its inhibitor, compstatin. *J Biol Chem*, 279, 54987-54995.

Lauri, G. and Bartlett, P. A. (1994) CAVEAT: A program to facilitate the design of organic molecules. *J Comput Aided Mol Des*, 8, 51-66.

Luty, B. A., Wasserman, Z. R., Stouten, P. F., Hodge, C. N., Zacharias, M., and McCammon, J. A. (1995) Molecular Mechanics/Grid Method for Evaluation of Ligand-Receptor Interactions. *J. Comput. Chem.* 16, 454-464.

Mallik, B., Katragadda, M., Spruce, L. A., Carafides, C., Tsokos, C. G., Morikis, D. and Lambris, J. D. (2005) Design and NMR characterization of active analogues of compstatin containing non-natural amino acids. *J Med Chem*, 48, 274-286.

McCoy, A. J., Grosse-Kunstleve, R. W., Storoni, L. C. and Read, R. J. (2005) Likelihood-enhanced fast translation functions. *Acta Crystallogr D Biol Crystallogr*, 61, 458-464.

Morikis, D., Assa-Munt, N., Sahu, A. and Lambris, J. D. (1998) Solution structure of Compstatin, a potent complement inhibitor. *Protein Sci*, 7, 619-627.

Morikis, D., Roy, M., Sahu, A., Troganis, A., Jennings, P. A., Tsokos, G. C. and Lambris, J. D. (2002) The structural basis of compstatin activity examined by structure-function-based design of peptide analogs and NMR. *J Biol Chem*, 277, 14942-14953.

Morikis, D., Soulika, A. M., Mallik, B., Klepeis, J. L., Floudas, C. A. and Lambris, J. D. (2004) Improvement of the anti-C3 activity of compstatin using rational and combinatorial approaches. *Biochem Soc Trans*, 32, 28-32.

Morris, G. M., Goodsell, D. S., Halliday, R. S., Huey, R., Hart, W. E., Belew, R. K., and Olson, A. J. (1998) Automated Docking Using a Lamarckian Genetic Algorithm and an Empirical Binding Free Energy Function. *J. Computational Chemistry*, 19, 1639-1662.

Nishida, N., Walz, T. and Springer, T. A. (2006) Structural transitions of complement component C3 and its activation products. *Proc Natl Acad Sci USA*, 103, 19737-19742.

Ponnuraj, K., Xu, Y., Macon, K., Moore, D., Volanakis, J. E. and Narayana, S. V. (2004) Structural analysis of engineered Bb fragment of complement factor B: insights into the activation mechanism of the alternative pathway C3-convertase. *Mol Cell*, 14, 17-28.

Sahu, A., Kay, B. K. and Lambris, J. D. (1996) Inhibition of human complement by a C3-binding peptide isolated from a phage-displayed random peptide library. *J Immunol*, 157, 884-891.

Sahu, A. and Lambris, J. D. (2000) Complement inhibitors: a resurgent concept in anti-inflammatory therapeutics. *Immunopharmacology*, 49, 133-148.

Sahu, A., Morikis, D. and Lambris, J. D. (2003) Compstatin, a peptide inhibitor of complement, exhibits species-specific binding to complement component C3. *Mol Immunol*, 39, 557-566.

Sahu, A., Soulika, A. M., Morikis, D., Spruce, L., Moore, W. T. and Lambris, J. D. (2000) Binding kinetics, structure-activity relationship, and biotransformation of the complement inhibitor compstatin. *J Immunol*, 165, 2491-2499.

Soulika, A. M., Holland, M. C., Sfyroera, G., Sahu, A. and Lambris, J. D. (2006) Compstatin inhibits complement activation by binding to the beta-chain of complement factor 3. *Mol Immunol*, 43, 2023-2029.

Soulika, A. M., Morikis, D., Sarrias, M. R., Roy, M., Spruce, L. A., Sahu, A. and Lambris, J. D. (2003) Studies of structure-activity relations of complement inhibitor compstatin. *J Immunol*, 171, 1881-1890.

Stouten, P. F., Froemmel, C., Nakamura, H., and Sander, C. (1993) An Effective Solvation Term Based on Atomic Occupancies for Use in Protein Simulations. *Molecular Simulation* 10, 97-120.

Thompson, J. D., Higgins, D. G. and Gibson, T. J. (1994) CLUSTAL W: improving the sensitivity of progressive multiple sequence alignment through sequence weighting, position-specific gap penalties and weight matrix choice. *Nucleic Acids Res*, 22, 4673-4680.

Vicatos S, Reddy B V, Kaznessis Y. (2005) Prediction of distant residue contacts with the use of evolutionary information. *Proteins* 58, 935-949.

Wallace, A. C., Laskowski, R. A. and Thornton, J. M. (1995) LIGPLOT: a program to generate schematic diagrams of protein-ligand interactions. *Protein Eng*, 8, 127-134.

Walport, M. J. (2001) Complement. First of two parts. *N Engl J Med*, 344, 1058-1066.

Wiesmann, C., Katschke, K. J., Yin, J., Helmy, K. Y., Steffek, M., Fairbrother, W. J., McCallum, S. A., Embuscado, L., DeForge, L., Hass, P. E. and van Lookeren Campagne, M. (2006) Structure of C3b in complex with CRIg gives insights into regulation of complement activation. *Nature*, 444, 217-220.

U.S. Pat. No. 6,319,897 to Lambris et al.
PCT Pub. No. WO99/13899
(PCT Pub. No. WO2004/026328

The present invention is not limited to the embodiments described and exemplified above, but is capable of variation and modification within the scope of the appended claims.

What is claimed:

1. A method for designing a complement inhibitor, the method comprising:
   (a) obtaining a monoclinic crystal in space group $P2_1$, having the unit cell dimension of a=85.8, b=124.7, c=127.4 Å, β=95.1°, of a complex consisting of C3c purified from human plasma and compstatin of SEQ ID NO:1 bound to the C3c at a compstatin binding location;

(b) determining the three dimensional structure of the complex using the crystal obtained in (a) by the X-ray diffraction method to obtain the atomic coordinates of the structure;

(c) providing on a computer the atomic coordinates of the three dimensional structure of the complex; and (d) utilizing a program operated by the computer to design a chemical compound predicted to bind to C3 or C3c at the compstatin binding location and inhibit proteolytic activation of C3.

2. The method of claim 1, wherein the designing involves de novo rational drug design.

3. The method of claim 2, wherein the rational drug design involves (i) identification of functional groups and/or small molecule fragments which can interact with sites in the compstatin binding location on the C3 or C3c, and (ii) linking the functional groups and/or small molecule fragments in a single compound.

4. The method of claim 1, wherein the designing involves modifying the compstatin peptide structure.

5. The method of claim 1, wherein the designing involves utilizing docking software and screening one or more databases for molecules that fit the compstatin binding location on the C3 or C3c.

6. The method of claim 1, further comprising: (e) synthesizing or obtaining the compound; and (f) evaluating the compound for its ability to perform one or more of (1) binding C3, (2) competing with the compstatin for binding C3, (3) inhibiting proteolytic activation of C3, or (4) inhibiting complement activation.

7. The method of claim 3, wherein the rational drug design is based on the hydrophobic interactions between one or more of residues Val-3, Trp-4 and Trp-7 of the compstatin of SEQ ID NO:1 and the C3 or C3c.

8. The method of claim 7, wherein the hydrophobic interaction is CH/π and sulfur-aromatic interactions between Trp-4 and Cys-12 of the compstatin comprising SEQ ID NO:1.

9. The method of claim 2, which comprises rational drug design based on one or more hydrogen bond interactions between the compstatin comprising SEQ ID NO: 1 and the C3c comprising SEQ ID NO:4, the one or more hydrogen bond interaction selected from the group consisting of:
- an N-terminal acetyl group of SEQ ID NO: 1 and Asn390 of SEQ ID NO:4;
- Ile1 of SEQ ID NO: 1 and Asn390 of SEQ ID NO:4;
- Trp4 of SEQ ID NO: 1 and Gly345 or Arg456 of SEQ ID NO:4;
- Gln5 of SEQ ID NO: 1 and Leu455 of SEQ ID NO:4;
- Gln5 of SEQ ID NO: 1 and Asp491 or Met457 of SEQ ID NO:4;
- Trp7 of SEQ ID NO: 1 and Met457 of SEQ ID NO:4; and
- His10 of SEQ ID NO: 1 and Asp491 of SEQ ID NO:4.

10. The method of claim 2, which comprises rational drug design based on one or more hydrophobic interactions between the compstatin comprising SEQ ID NO: 1 and the C3c comprising SEQ ID NO:4, the one or more hydrophobic interactions selected from the group consisting of:
- Cyst of SEQ ID NO: 1 and Asn390 of SEQ ID NO:4;
- Val3 of SEQ ID NO: 1 and Met346, Pro347, Leu454 or Arg456 of SEQ ID NO:4;
- Trp4 of SEQ ID NO: 1 and Pro393 or His 392 of SEQ ID NO:4;
- Gln5 of SEQ ID NO: 1 and Arg456 of SEQ ID NO:4;
- Trp7 of SEQ ID NO: 1 and Leu455, Arg459, Glu462 or Gly489 of SEQ ID NO:4;
- Gly8 of SEQ ID NO: 1 and Asp491 of SEQ ID NO:4; and
- His10 of SEQ ID NO: 1 and Asp491 or Leu 492 of SEQ ID NO:4.

11. The method of claim 2, which comprises rational drug design based on one or more hydrogen bond interactions within the compstatin comprising SEQ ID NO:1 or SEQ ID NO:2 selected from:
- Val3 and His10 of SEQ ID NO:1 or SEQ ID NO:2;
- Gln5 and Val3 of SEQ ID NO:1 or SEQ ID NO:2;
- Cys12 and Val3 of SEQ ID NO: 1 or SEQ ID NO:2;
- Thr13 and Cys12 of SEQ ID NO:1 or SEQ ID NO:2; and
- $NH_2$14 and Cys12 of SEQ ID NO:1 or SEQ ID NO:2.

* * * * *